(12) United States Patent
Lyon et al.

(10) Patent No.: US 11,471,140 B2
(45) Date of Patent: Oct. 18, 2022

(54) VERIVAS RAPID VEIN HARVESTER

(71) Applicants: Ross Traut Lyon, Fontana, WI (US); Alexander Derek. Crich, Huntington Beach, CA (US); John-Anthony Isaac Fraga, Harlingen, TX (US)

(72) Inventors: Ross Traut Lyon, Fontana, WI (US); Alexander Derek. Crich, Huntington Beach, CA (US); John-Anthony Isaac Fraga, Harlingen, TX (US)

(73) Assignee: VERIVAS SOLUTIONS INC., Stamford, CT (US)

( * ) Notice: Subject to any disclaimer, the term of this patent is extended or adjusted under 35 U.S.C. 154(b) by 262 days.

(21) Appl. No.: 16/858,203

(22) Filed: Apr. 24, 2020

(65) Prior Publication Data
US 2021/0330308 A1 Oct. 28, 2021

(51) Int. Cl.
*A61B 17/00* (2006.01)
*A61L 27/50* (2006.01)
(Continued)

(52) U.S. Cl.
CPC .... *A61B 17/00234* (2013.01); *A61L 27/3625* (2013.01); *A61L 27/507* (2013.01);
(Continued)

(58) Field of Classification Search
CPC ........ A61B 17/00008; A61B 17/00234; A61B 2017/00013; A61B 2017/00331;
(Continued)

(56) References Cited

U.S. PATENT DOCUMENTS 4,793,346 A * 12/1988 Mindich .......... A61B 17/00008
   606/180
5,373,840 A * 12/1994 Knighton ............... A61B 1/018
   600/156
(Continued)

FOREIGN PATENT DOCUMENTS

GB 2082459 A 3/1982

OTHER PUBLICATIONS

Hill BB, Faruqi RM, Arko FR, Zarins CK, Fogarty TJ. "Over-the-Wire" Inversion Saphenectomy: A Simple, Minimally Invasive Vein Harvesting Technique for Arterial Bypass. Journal of Endovascular Therapy. 2005;12(3):394-400. doi:10.1583/04-1350R.1, Stanford, CA, USA.
(Continued)

*Primary Examiner* — Ryan J. Severson

(57) ABSTRACT

An apparatus for harvesting a subcutaneous blood vessel is disclosed. The apparatus comprises a guidewire with an angled tip, an intra-vascular catheter to receive the guidewire and having a lateral orifice to allow the angled tip thereof to perforate the subcutaneous blood vessel. The apparatus further comprises a flexible pulling device having a pair of circumferential grooves, one adjacent to each end thereof, to allow for securing the subcutaneous blood vessel thereat; and a flexible pushing device having a concave-cup shape at a distal end thereof to facilitate pushing of the subcutaneous blood vessel secured with one of the pair of circumferential grooves of the flexible pulling device. The flexible pulling device and the flexible pushing device are operable in conjunction to cause inversion and eversion and separation from the surrounding tissues of the subcutaneous blood vessel for removal and harvesting thereof.

20 Claims, 12 Drawing Sheets

US 11,471,140 B2

Page 2

(51) Int. Cl.
    *A61L 27/36*     (2006.01)
    *A61B 17/12*     (2006.01)
    *A61M 25/09*     (2006.01)

(52) U.S. Cl.
    CPC ............... *A61B 2017/00331* (2013.01); *A61B 2017/00778* (2013.01); *A61B 2017/00942* (2013.01); *A61B 2017/00969* (2013.01); *A61B 2017/12004* (2013.01); *A61M 25/09041* (2013.01)

(58) Field of Classification Search
    CPC ........... A61B 2017/00778; A61B 2017/00942; A61B 2017/00969; A61B 2017/12004; A61F 2/062; Y10S 623/916; A61L 27/3625; A61L 27/507
    See application file for complete search history.

(56) References Cited

U.S. PATENT DOCUMENTS

| | | | | |
|---|---|---|---|---|
| 5,593,418 | A * | 1/1997 | Mollenauer | A61B 17/22032 606/198 |
| 5,695,514 | A * | 12/1997 | Chin | A61B 17/00008 606/190 |
| 5,797,947 | A * | 8/1998 | Mollenauer | A61B 17/00008 606/108 |
| 5,836,945 | A * | 11/1998 | Perkins | A61B 17/00008 606/41 |
| 5,843,104 | A | 12/1998 | Samuels | |
| 5,873,889 | A * | 2/1999 | Chin | A61B 17/00008 606/190 |
| 5,899,913 | A * | 5/1999 | Fogarty | A61B 17/00008 606/190 |
| 5,902,316 | A * | 5/1999 | Mollenauer | A61M 25/0119 606/190 |
| 5,968,065 | A * | 10/1999 | Chin | A61B 17/11 606/190 |
| 5,970,982 | A * | 10/1999 | Perkins | A61B 17/00008 606/159 |
| 5,976,168 | A * | 11/1999 | Chin | A61B 17/320016 606/190 |
| 6,030,396 | A | 2/2000 | Samuels | |
| 6,036,713 | A * | 3/2000 | Kieturakis | A61B 17/3439 606/190 |
| 6,077,289 | A * | 6/2000 | Mollenauer | A61B 17/00008 606/190 |
| 6,520,975 | B2 * | 2/2003 | Branco | A61B 17/00008 600/114 |
| 6,551,314 | B1 | 4/2003 | Fogarty | |
| 6,558,313 | B1 * | 5/2003 | Knighton | A61B 17/00008 600/36 |
| 6,887,251 | B1 * | 5/2005 | Suval | A61B 17/00008 606/159 |
| 7,074,220 | B2 | 7/2006 | Fogarty | |
| 8,480,696 | B2 * | 7/2013 | Clague | A61B 17/00008 606/159 |
| 10,064,611 | B2 * | 9/2018 | Ross | A61B 17/00008 |
| 10,507,012 | B2 * | 12/2019 | Knighton | A61B 17/00008 |
| 10,575,835 | B2 * | 3/2020 | Sharma | A61B 18/1482 |
| 10,687,793 | B2 * | 6/2020 | Gallagher | A61B 90/30 |
| 2004/0049208 | A1 * | 3/2004 | Hill | A61B 17/00008 606/145 |
| 2004/0092990 | A1 * | 5/2004 | Opie | A61B 17/00008 606/167 |
| 2004/0122458 | A1 * | 6/2004 | Opie | A61B 17/00008 606/159 |
| 2005/0004586 | A1 * | 1/2005 | Suval | A61B 17/00008 606/159 |
| 2005/0273125 | A1 * | 12/2005 | Opie | A61B 17/00008 606/159 |
| 2007/0005084 | A1 * | 1/2007 | Clague | A61B 17/00008 606/159 |
| 2008/0161843 | A1 * | 7/2008 | Clague | A61B 17/32053 604/509 |
| 2010/0305594 | A1 * | 12/2010 | Opie | A61B 17/00008 606/170 |
| 2013/0282009 | A1 * | 10/2013 | Knodel | A61B 18/1482 606/47 |
| 2021/0330308 | A1 * | 10/2021 | Lyon | A61L 29/14 |

OTHER PUBLICATIONS

Goren G., Yellin AE., Invaginated axial saphenectomy by a semi-rigid stripper: perforate-invaginate stripping. Journal of vascular surgery., 1994, vol. 20(6), p. 970-977. Encino, CA USA.

* cited by examiner

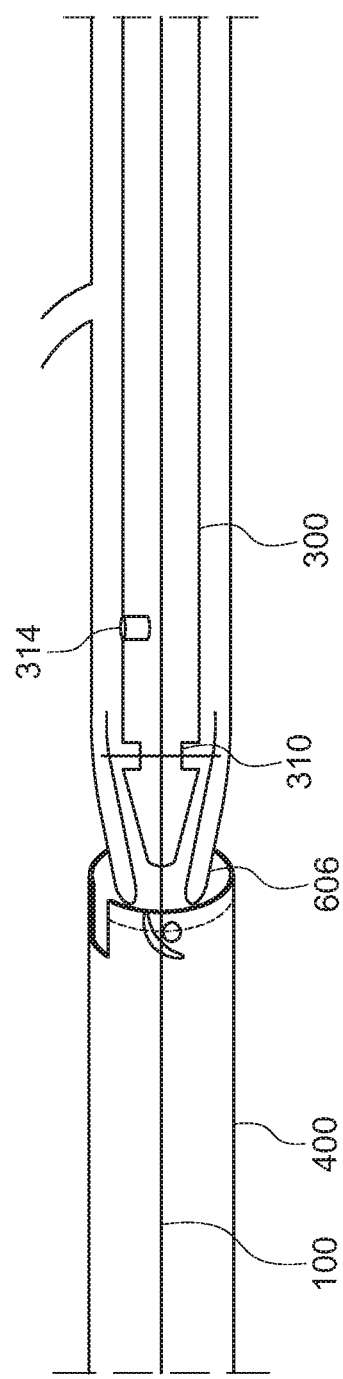

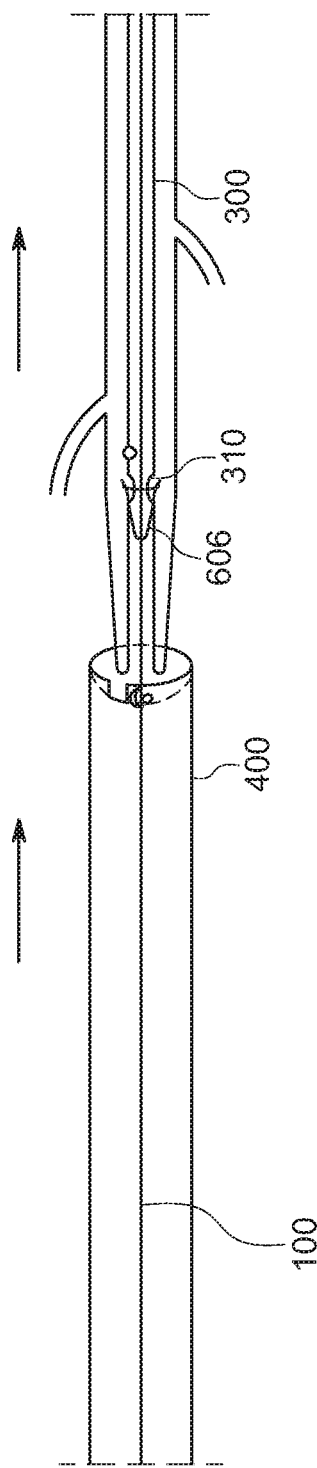

VERIVAS RAPID VEIN HARVESTER

CROSS-REFERENCE TO RELATED APPLICATIONS

This application claims priority from U.S. Provisional Application No. 62/838,375 filed Apr. 25, 2019, titled "Verivas Rapid Vein Harvester", the content of which is incorporated herein.

FIELD OF THE PRESENT DISCLOSURE

The present disclosure relates generally to medical apparatus and methods, and more specifically, to apparatus and method for vascular surgery, including intraluminal vein harvesting of a subcutaneous blood vessel.

BACKGROUND

Arterial occlusive disease, specifically coronary artery disease and peripheral artery disease involves vessels of various organs being damaged or obstructed by atherosclerotic plaques containing cholesterol, lipoid material, lipophages, and other materials or by traumatic injuries. When severely damaged or obstructed, one or more of the vessels can be bypassed during an arterial bypass procedure. The saphenous vein is a subcutaneous vein which is often harvested and used for coronary artery bypass grafting, infra-inguinal bypass grafting and vein-vein bypass grafting. Other vessels may also be used including the cephalic and lesser saphenous veins, the internal mammary artery and the radial artery. Vessels are also commonly removed because they are abnormal, diseased or infected and for cosmetic reasons. Conventionally, it has been necessary to make an incision along the full length of the vein or artery being removed or harvested for use as a bypass conduit. The vein is then freed by severing and ligating the branches of the vein, after which the section of the vein can be removed from the patient and used or discarded. The full-length incision must then be closed, for example by suturing and/or stapling. The harvesting of the vein in this manner has significant associated risks and can also leave disfiguring scars which are undesirable for many reasons. Additionally, the large incisions may not heal properly, especially with those patients who have poor circulation in their extremities.

Less invasive procedures have been devised, and surgical devices and techniques now exist that allow the saphenous vein to be harvested through one or more small, transverse incisions along the length of the vein, generally using an endoscope. Endoscopic procedures yield reduced wound complications and superior cosmetic results compared with traditional methods of vein harvesting. However, this procedure requires considerable manipulation of the vein, has a high conversion rate when visualization is obscured by bleeding or too difficult. Further, it is generally tedious, time consuming, and highly technical, requiring a substantial learning curve for the surgeon, some of whom never fully master the technique.

Therefore, it would be desirable to have means for harvesting a vessel section that overcome the aforementioned and other disadvantages. The present invention discloses an apparatus and a method which provide a minimally invasive and simple rapid procedure for removing/harvesting subcutaneous blood vessels. Additional advantages and novel features of the present invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

SUMMARY

In one aspect, an apparatus for harvesting of a subcutaneous blood vessel is disclosed. The apparatus comprises a guidewire having a body with a proximal end and a distal end. The guidewire comprises an angled tip extending from the distal end of the body. The apparatus also comprises an intra-vascular catheter adapted to be inserted into the subcutaneous blood vessel and to receive the guidewire, extending therein from the proximal end to the distal end thereof. The intra-vascular catheter has a lateral orifice near a distal end thereof to allow for exiting of the guidewire therefrom and the angled tip thereof to perforate the subcutaneous blood vessel at a determined longitudinal location and radial orientation and to be directed to skin surface above the subcutaneous blood vessel to be retrieved through the skin surface. The apparatus further comprises a flexible pulling device comprising a cylindrical body with a guidewire lumen and adapted to be co-axially arranged over the guidewire by receiving the guidewire in the guidewire lumen therein to allow for advancement and retraction thereof over the guidewire. The flexible pulling device has a pair of circumferential grooves, one adjacent to each end thereof, to allow for securing the subcutaneous blood vessel thereat. The apparatus further comprises a flexible pushing device comprising a cylindrical body with a guidewire lumen and adapted to be co-axially arranged over the guidewire by receiving the guidewire in the guidewire lumen therein to allow for advancement and retraction thereof over the guidewire. The flexible pushing device has a concave-cup shape at a distal end thereof to keep the flexible pushing device external to the subcutaneous blood vessel and to facilitate pushing of the subcutaneous blood vessel secured to one of the pair of circumferential grooves of the flexible pulling device. The flexible pulling device and the flexible pushing device are operable in conjunction to cause inversion and eversion of the subcutaneous blood vessel for removal or harvesting without exposing an internal surface thereof.

In one or more embodiments, the guidewire comprises one or more marks to indicate the radial orientation thereof and a longitudinal positioning of the angled tip of the guidewire with respect to the lateral orifice of the intravascular catheter.

In one or more embodiments, the guidewire comprises one or more circumferential marks to indicate the longitudinal positioning of the guidewire.

In one or more embodiments, the intra-vascular catheter further comprises an angled movable flap, associated with the lateral orifice, for directing the guidewire or fluid to exit through the lateral orifice therein.

In one or more embodiments, the guidewire lumen in the flexible pulling device is located centrally inside the flexible pulling device.

In one or more embodiments, the flexible pulling device has symmetrical tapered portions at each end thereof, with each of the pair of circumferential grooves being located adjacent to the tapered portions at each end thereof.

In one or more of the embodiments, the flexible pulling device further comprises two or more lateral holes connecting the central guidewire lumen to the outside of the catheter to allow ingress and egress of fluid and/or air.

In one or more embodiments, the flexible pushing device further comprises a fluid lumen extending between the guidewire lumen and a body of the intravascular catheter to facilitate movement of air and fluids therein and so at to facilitate inversion and eversion of the subcutaneous blood vessel.

In one or more embodiments, the fluid lumen in the flexible pushing device is arranged concentric to the guidewire lumen.

In one or more embodiments, the fluid lumen in the flexible pushing device is arranged adjacent to the guidewire lumen.

In one or more embodiments, the flexible pushing device further comprises threads provided at a proximal end thereof to allow for a removable connection to an external adapter for infusion of fluids through the fluid lumen in the flexible pushing device for delivery to the site at which the subcutaneous blood vessel is harvested.

In one or more embodiments, the flexible pushing device further comprises a notch located laterally at the distal end thereof to engage side branches of the subcutaneous blood vessel, and a flattened portion at a proximal end thereof to indicate radial orientation of the notch so as to facilitate positioning and engagement of the notch with the side branches of the subcutaneous blood vessel.

In one or more embodiments, the apparatus further comprises a flexible cutting sheath device adapted to be introduced and to slide over the flexible pushing device. The flexible cutting sheath device comprises a notch with sharpened side edges at a distal end thereof to transect the side branches of the subcutaneous blood vessel engaged in the notch of the flexible pushing device by rotation the flexible cutting sheath device and the flexible pushing device in opposing directions.

In one or more embodiments, the flexible pushing device further includes one or more circumferential marks thereon to indicate longitudinal positioning and alignment of the distal end of the flexible pushing device with respect to the distal end of the flexible cutting sheath device.

In one or more embodiments, the flexible pushing device further comprises one or more longitudinal marks and the flexible cutting sheath device comprises one or more longitudinal marks. A radial orientation of the flexible cutting sheath device is indicated by determining a relative position of at least one of a notch disposed at a proximal end of the flexible cutting sheath device or the one or more longitudinal marks of the flexible cutting sheath device with respect to the one or more longitudinal marks of the flexible pushing device.

In one or more embodiments, the body of the guidewire is coated with hydrophilic coating.

In one or more embodiments, the angled tip extends at an angle in the range of 50 to 60 degrees with respect to a longitudinal portion of the body.

In another aspect, a method for harvesting of a subcutaneous blood vessel utilizing the apparatus as described above is disclosed. The method comprises the steps of:
(i) identifying the subcutaneous blood vessel to be removed/harvested by inspection or a use of transcutaneous ultrasound imaging;
(ii) making a distal incision in skin surface over a distal end portion of the subcutaneous blood vessel to be harvested;
(iii) transecting the subcutaneous blood vessel exposed through the distal incision and ligating the distal end portion of the subcutaneous blood vessel;
(iv) inserting an intra-vascular catheter, over a vascular guidewire, if desired, into the subcutaneous blood vessel through the distal end portion of the subcutaneous blood vessel and advancing the intra-vascular catheter towards a proximal end portion of the subcutaneous blood vessel;
(v) receiving a guidewire having an angled tip inside the intra-vascular catheter, extending therein from the distal end portion to the proximal end portion of the subcutaneous blood vessel;
(vi) positioning a lateral orifice in the intra-vascular catheter at the proximal end portion of the subcutaneous blood vessel, with the lateral orifice facing anteriorly toward the skin surface;
(vii) exiting the distal end of the guidewire from the lateral orifice in the intra-vascular catheter to cause the angled tip of the guidewire to perforate the subcutaneous blood vessel at a determined longitudinal and radial orientation and making a proximal incision in the skin surface to allow the angled tip of the guidewire to exit therefrom;
(viii) withdrawing the intra-vascular catheter;
(ix) advancing a flexible pulling device over the guidewire from the proximal end of the guidewire to the distal end thereof until a distal end of the flexible pulling device reaches near the proximal incision in the skin surface to be pulled out therefrom;
(x) transecting and ligating the proximal end portion of the subcutaneous blood vessel;
(xi) securing the distal end portion of the subcutaneous blood vessel to a circumferential groove near a proximate end of the flexible pulling device;
(xii) pulling the flexible pulling device towards the proximal end portion of the subcutaneous blood vessel causing inversion thereof;
(xiii) advancing a flexible pushing device over the guidewire from the proximal end of the guidewire to the distal end thereof to facilitate pushing of a folded edge of an inverted end of the subcutaneous blood vessel secured with the circumferential groove of the flexible pulling device towards the proximal incision, while keeping the flexible pushing device external to subcutaneous blood vessel being harvested;
(xiv) introducing a fluid inside a fluid lumen of the flexible pushing device to facilitate a separation of the subcutaneous blood vessel from surrounding tissues; and
(xv) advancing a flexible cutting sheath device from the distal incision towards the proximal end portion of the subcutaneous blood vessel by sliding over the flexible pushing device to transect the side branches of the subcutaneous blood vessel engaged in a notch of the flexible pushing device by a sharpened notch of the flexible cutting sheath device by rotation of the flexible cutting sheath device and the flexible pushing device in opposing directions, in order to facilitate harvesting of the subcutaneous blood vessel.

In one or more embodiments, the method further comprises the steps of:
(xvi) everting the inverted portion of the subcutaneous blood vessel by pulling the flexible pulling device back over the guidewire towards the distal incision;

(xvii) disengaging the distal end portion of the subcutaneous blood vessel from the circumferential groove near the proximate end of the flexible pulling device;
(xviii) securing the proximal end portion of the subcutaneous blood vessel to a circumferential groove near the distal end of the flexible pulling device;
(xix) further pulling the flexible pulling device towards the distal end portion of the subcutaneous blood vessel causing inversion thereof;
(xx) advancing the flexible pushing device over the guidewire from the distal end of the guidewire towards the proximal end thereof to invert the proximal end of the subcutaneous blood vessel, and keeping the flexible pushing device external to the inverted subcutaneous blood vessel being harvested;
(xxi) advancing the flexible cutting sheath device from the proximal incision towards the distal end portion of the subcutaneous blood vessel by sliding over the flexible pushing device to transect the side branches of the proximal portion of the subcutaneous blood vessel engaged in the notch of the flexible pushing device by rotation of the flexible cutting sheath device and the flexible pushing device in opposing directions;
(xxii) securing the distal end portion of the subcutaneous blood vessel to the circumferential groove near the distal end of the flexible pulling device; and
(xxiii) removing the flexible pulling for removing the subcutaneous blood vessel, separated from the surrounding tissues, from the patient through the distal incision.

In one or more embodiments, the method further comprises the steps of:
(xxiv) advancing the intra-vascular catheter over the guidewire; and
(xxv) introducing one or more of fluids and medications in the intra-vascular catheter for flushing of or otherwise altering the site of the subcutaneous blood vessel.

In one or more embodiments, the step (xiv) comprises introducing the fluid through the fluid lumen in the flexible pushing device by attaching a fluid source via an external adapter connected to a threads provided at a proximal end of the flexible pushing device.

In one or more embodiments, the step (xv) comprises determining at least one of relative position of the notch and proximal end of the flexible cutting sheath device with respect to one or more longitudinal and circumferential marks in the flexible pushing device to indicate a radial orientation and longitudinal positioning of the flexible cutting sheath device relative to the flexible pushing device.

The features and advantages described in this disclosure and in the following detailed description are not all-inclusive. Many additional features and advantages will be apparent to one of ordinary skill in the relevant art in view of the drawings, specification, and claims hereof. Moreover, it should be noted that the language used in the specification has been principally selected for readability and instructional purposes and may not have been selected to delineate or circumscribe the inventive subject matter; reference to the claims is necessary to determine such inventive subject matter.

BRIEF DESCRIPTION OF THE DRAWINGS

For a more complete understanding of example embodiments of the present disclosure, reference is now made to the following descriptions taken in connection with the accompanying drawings in which:

FIGS. 6A-6G illustrate diagrammatic depictions of various stages involved in utilization of the said apparatus for harvesting of the subcutaneous blood vessel, in accordance with one or more embodiments of the present disclosure.

DETAILED DESCRIPTION

Figure 1A:
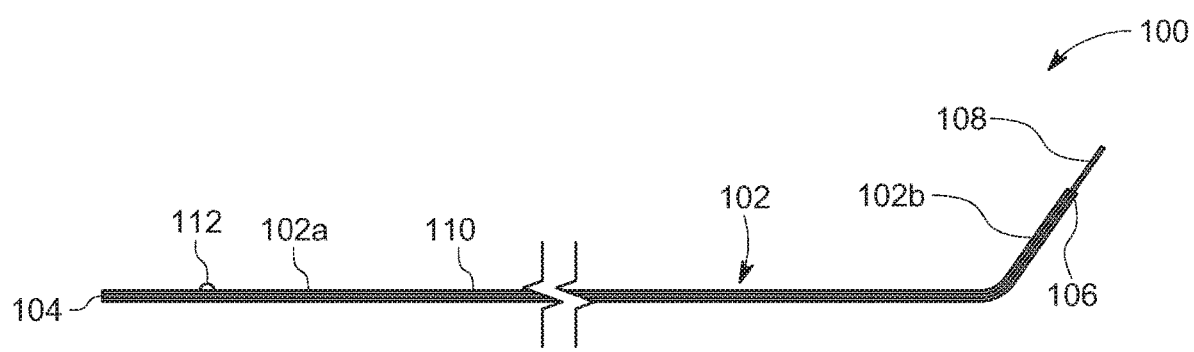
FIGS. 1A-1B illustrate diagrammatic views of a guidewire of an apparatus for harvesting of a subcutaneous blood vessel, in accordance with an example embodiment of the present disclosure.

In the following description, for purposes of explanation, numerous specific details are set forth in order to provide a thorough understanding of the present disclosure. It will be apparent, however, to one skilled in the art that the present disclosure can be practiced without these specific details. In other instances, apparatuses and methods are shown in block diagram form only in order to avoid obscuring the present disclosure.

Embodiments of the present invention are hereafter described in detail with reference to the accompanying Figures. Although the invention has been described and illustrated with a certain degree of particularity, it is understood that the present disclosure has been made only by way of example and that numerous changes in the combination and arrangement of parts can be resorted to by those skilled in the art without departing from the spirit and scope of the invention.

The following description with reference to the accompanying drawings is provided to assist in a comprehensive understanding of exemplary embodiments of the present invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Like numbers refer to like elements throughout. In the figures, the sizes of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. Thus, for example, a reference to "a component surface" includes reference to one or more of such surfaces.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be also understood that when an element is referred to as being "on," "attached" to, "connected" to, "coupled" with, "contacting", "mounted" etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of reasonable skill in the relevant art that references to a structure or a feature that is "adjacent" to another feature may have portions that overlap or underlie that feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of a device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

Included in the description are flowcharts depicting examples of the methodology which may be used to utilize the disclosed apparatus for harvesting of a subcutaneous blood vessel. Accordingly, blocks of the flowchart illustrations support combinations of means for performing the specified functions and combinations of steps for performing the specified functions. It will also be understood that each block of the flowchart illustrations, and combinations of blocks in the flowchart illustrations, can be implemented by special purpose hardware and/or computer systems that perform the specified functions or steps, or combinations of special purpose hardware and computer instructions.

Upon reading this disclosure, those of skill in the art will appreciate still additional alternative structural and functional designs for the disclosed apparatus for harvesting of a subcutaneous blood vessel through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope of the invention.

The present disclosure provides an apparatus for removing/harvesting of a subcutaneous blood vessel. The present apparatus is in the form of a kit including multiple components which works in combination to achieve the given purpose. It is to be understood that the said subcutaneous blood vessel is harvested by removing one or more sections of a tissue structure from a patient's body. The harvested subcutaneous blood vessel may be used in another part of the patient's body, may be transplanted into a second patient's body or may be discarded. Although the invention herein has been discussed in terms of harvesting the subcutaneous blood vessel it should be understood that the apparatus and method described are equally applicable to harvesting other solid or cylindrical tubular tissue structure. That is, although the apparatus of the present disclosure has been described in terms of harvesting a "subcutaneous blood vessel," the disclosed apparatus can generally be used for harvesting other types of blood vessels, or any tissue structure such as ureters, bile ducts, or any other similar tissue formation which is generally tubular in structure and capable of being separated from surrounding tissue. Hereinafter, the terms "subcutaneous blood vessel," "blood vessel," and "vein" have been interchangeably used without any limitations.

Referring to FIG. 1A, illustrated is a diagrammatic side view of a guidewire 100 for the said apparatus. The guidewire 100 includes a body 102. As may be seen, the body 102 of the guidewire 100 includes a longitudinal portion 102a and an angled portion 102b. The body 102 has a proximal end 104 and a distal end 106. The body 102 of the guidewire 100 is coated with a hydrophilic coating 110. The hydrophilic coating 110 forms a thin layer over the body 102 of the guidewire 100. In an example, the body 102 of the guidewire 100 is made of stainless steel or Nickel and Titanium alloy, also known as Nitinol, and is covered with polyurethane containing tungsten and a hydrophilic polymer coating for complete, low friction maneuverability. The guidewire 100 also includes an angled tip 108 extending from the distal end 106 of the body 102. In present examples, the angled tip 108 may not be provided with the hydrophilic coating. Herein, the angled tip 108 is in the form of a sharp tip capable of puncturing veins and other soft tissues in human body. In some examples, the body 102 may have a flexible portion of about 6 cm at the proximal end 104 thereof.

The guidewire 100 is capable of extending from a proximal location to a spaced-apart distal location along a vein. The guidewire 100, or specifically the longitudinal portion 102a of the body 102 of the guidewire 100, will typically have a length in the range from 80 cm to 200 cm (preferably about 100 cm) and a diameter in the range from 0.2 mm to 0.9 mm (usually 0.035"). Further, the angled portion 102b may have a length of about 2 to 5 cm (usually about 3 cm), and the uncovered tip 108 may have a length of about 1 cm. In an embodiment, the angled tip 108 extends at an angle in the range of 50 to 60 degrees with respect to the longitudinal portion 102a of the body 102, in the guidewire 100. Preferably, the angled tip 108 extends at an angle of 55 degrees with respect to the longitudinal portion 102a of the body 102. It may be appreciated that the bend for the angled tip 108 may be gradual, in some examples. It may be appreciated that the given dimensions are exemplary only, and shall not be construed as limiting to the embodiments of the present disclosure.

Figure 1B:
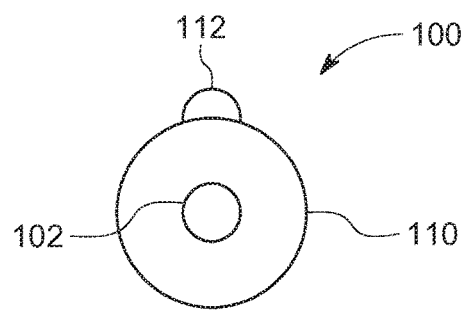

Referring to FIG. 1B, illustrated is a front planar view of the guidewire 100. As illustrated, the guidewire 100 comprises one or more marks 112 to indicate the radial orientation thereof. In one example, the said one or more marks 112 may be in the form of reference points or dots provided at a particular radial or circumferential orientation on an outer surface of the body 102 of the guidewire 100. In another example, one or more marks 112 may be in the form of a reference line extending from the proximal end 104 to the distal end 106 on the outer surface of the body 102 of the guidewire 100. It may be appreciated that other possible markings may be contemplated, such as, but not limited to, etchings or the like, without departing from the scope and the spirit of the present disclosure.

Figure 2A:
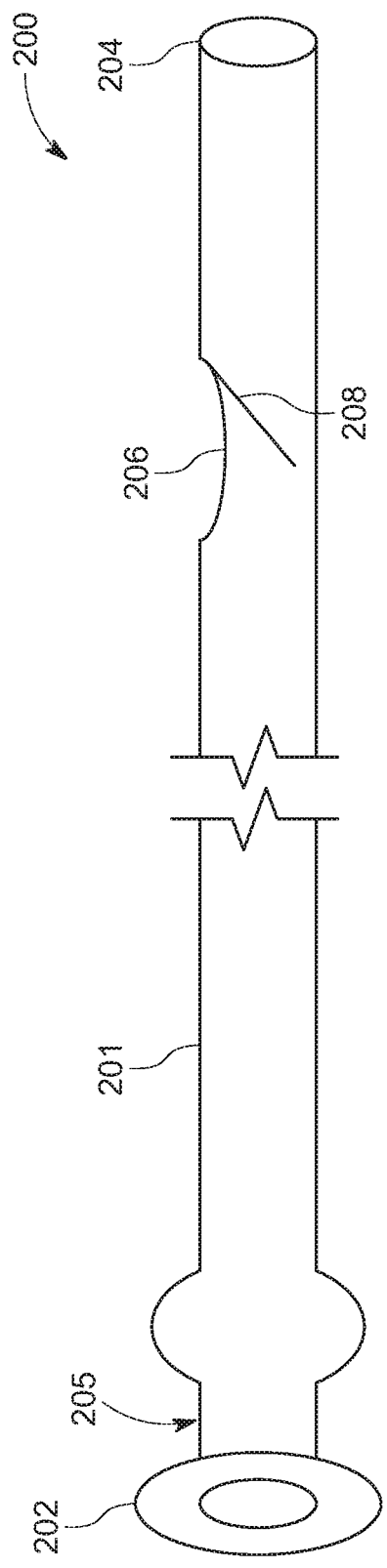
FIGS. 2A-2B illustrate diagrammatic views of an intra-vascular catheter of the said apparatus, in accordance with an example embodiment of the present disclosure.
Figure 2B:
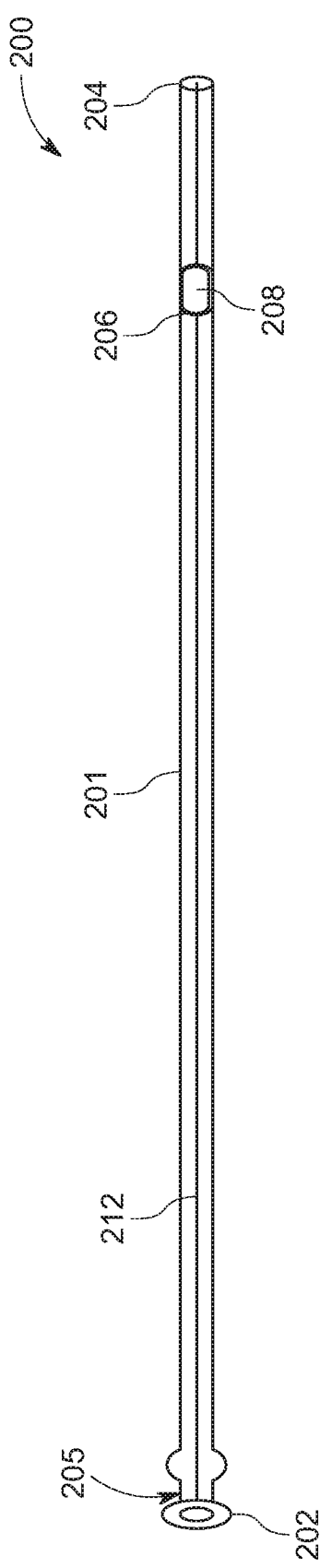

Referring now to FIGS. 2A and 2B in combination, illustrated are planar views of an intra-vascular catheter 200 for the said apparatus. The intra-vascular catheter 200 (hereinafter, sometimes, simply referred to as "catheter 200") is adapted to be inserted into the subcutaneous blood vessel to be harvested. In one example, the catheter 200 may be inserted into the subcutaneous blood vessel through a distal incision in a skin surface at a distal end portion of the subcutaneous blood vessel. The catheter 200 has a cylindrical body 201. The body 201 of the catheter 200 has a proximal end 202 and a distal end 204. The catheter 200 is further adapted to receive the guidewire 100 therein. For this purpose, the catheter 200 may, generally, be a hollow cylindrical structure. The guidewire 100 extends from the proximal end 104 to the distal end 106 thereof inside the catheter 200. In an example, the catheter 200 may have a radio opaque and an echogenic body to ensure visibility of the guidewire 100 therein. In some examples, the catheter 200 may further have receptacle 205 at the proximal end 202 to allow receiving and holding an external adapter, such as, a luer lock.

According to embodiments of the present disclosure, the intra-vascular catheter 200 has a lateral orifice 206 near the distal end 204 thereof. The lateral orifice 206 allows or provides a passage for exiting of the guidewire 100 therefrom. In particular, the angled tip 108 of the guidewire 100 exits through the lateral orifice 206 in the catheter 200. In an embodiment, the intra-vascular catheter 200 further comprises an angled movable flap 208. The angled movable flap 208 is associated with the lateral orifice 206. The angled movable flap 208 assists with directing the guidewire 100, or specifically the angled tip 108 thereof, to exit through the lateral orifice 206. In an example, the catheter 200 may have a length of about 60 cm and the angled movable flap 208 may be located at about 5 cm inwards from the distal end 204 of the catheter 200. Further, the angled movable flap 208 may have a width of about 80 percent of an inner diameter of the catheter 200.

In an embodiment, the intra-vascular catheter 200 further comprises attachment means 210 located at the proximal end 202 thereof. The attachment means 210 may be in the form of threads or the like, which allow for attachment of an external adapter such as a luer lock or a Tuohy Borst adapter, onto which, in turn, a syringe or the like may be attached for infusing of fluids inside the catheter 200. The fluids introduced can help with the harvesting procedure. Herein, the angled movable flap 208 may also help with directing any fluids introduced into the catheter 200 to exit therefrom, for example at a desired site of harvesting of the subcutaneous blood vessel.

Further, in an embodiment, the intra-vascular catheter 200 further comprises one or more marks 212 to indicate a longitudinal position and a radial orientation thereof. In one example, the said one or more marks 212 may be in the form of reference points or dots provided at a particular radial or circumferential orientation on an outer surface of the catheter 200. In another example, one or more marks 212 may be in the form of a reference line extending from the proximal end 202 to the distal end 204 of the catheter 200. It may be appreciated that other possible markings may be contemplated, such as, but not limited to, etchings or the like, without departing from the scope and the spirit of the present disclosure. Using the said one or more marks 212, the catheter 200 can be located at a desired longitudinal position and radial orientation inside the human body while harvesting the vein, such that the angled tip 108 of the guidewire 100 is able to perforate the subcutaneous blood vessel at the determined longitudinal and radial orientation in order to be directed to skin surface above the subcutaneous blood vessel to be retrieved through the skin surface, such as a proximal incision in the human body.

Figure 3:
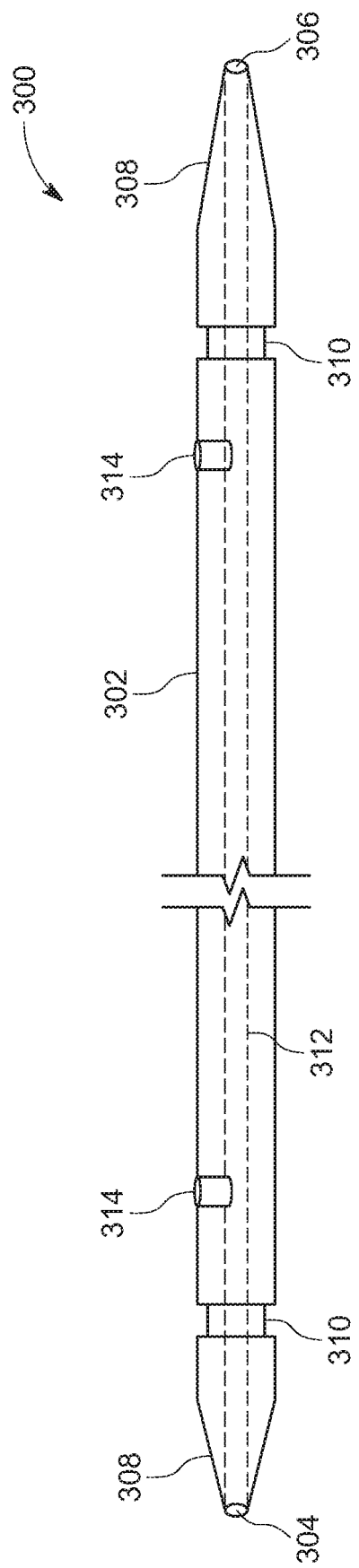
FIG. 3 illustrates a diagrammatic view of a flexible pulling device of the said apparatus, in accordance with one or more embodiments of the present disclosure.

Referring to FIG. 3, illustrated is a flexible pulling device 300 to be used as a component of the said apparatus. The flexible pulling device 300 comprises a cylindrical body 302. The body 302 of the flexible pulling device 300 may be made of any suitable surgical material as known in the art. In general, the flexible pulling device 300 is symmetrical, that is, the flexible pulling device 300 has a symmetrical body 302. The body 302 of the flexible pulling device 300 has a proximal end 304 and a distal end 306. Further, the body 302 has symmetrical tapered portions 308 at each end thereof. The tapered portions 308 helps with insertion of the flexible pulling device 300 inside the vein as required. Further, the flexible pulling device 300 includes a pair of circumferential grooves 310. Each one of the circumferential grooves 310 is adjacent to one of the two ends 304, 306 of the body 302 of the flexible pulling device 300. As may be seen, each of the pair of circumferential grooves 310 is located adjacent to the tapered portions 308 at each end 304, 306 of the flexible pulling device 300. The circumferential grooves 310, in the flexible pulling device 300, allow for securing the subcutaneous blood vessel thereat, for harvesting of the subcutaneous blood vessel.

The body 302 of the flexible pulling device 300 includes a guidewire lumen 312. The guidewire lumen 312, in the flexible pulling device 300, is located centrally inside the body 302 of the flexible pulling device 300. The guidewire lumen 312 is generally in the form of a narrow cylindrical tube with sufficient diameter to receive the guidewire 100 therein. When the flexible pulling device 300 is inserted into the vein with the guidewire 100 therein, the flexible pulling device 300 is adapted to be co-axially arranged over the guidewire 100 by receiving the guidewire 100 in the guidewire lumen 312 therein. This allows for advancement and retraction of the flexible pulling device 300 over the guidewire 100 when inserted inside the human body. In some embodiments, the flexible pulling device 300 further includes side holes 314 in the body 302 which provides access to the guidewire lumen 312, for example, for ingress and egress of fluid or air so as to not restrict the inversion or eversion of the blood vessel being harvested.

In an example, the flexible pulling device 300 may have a length of about 60 cm and a diameter of about 4 mm. The tapered portions 308 may extend to a length of about 3 cm from the respective proximal end 304 and the distal end 306. Also, the guidewire lumen 312 may have a diameter of at least greater than 0.035 in to receive and allow for movement over the guidewire 100. Further, the side holes 314 on the body 302 of the flexible pulling device 300 may have a size of about 1 mm. It may be appreciated that the given dimensions are exemplary only, and shall not be construed as limiting to the embodiments of the present disclosure.

Figure 4A:
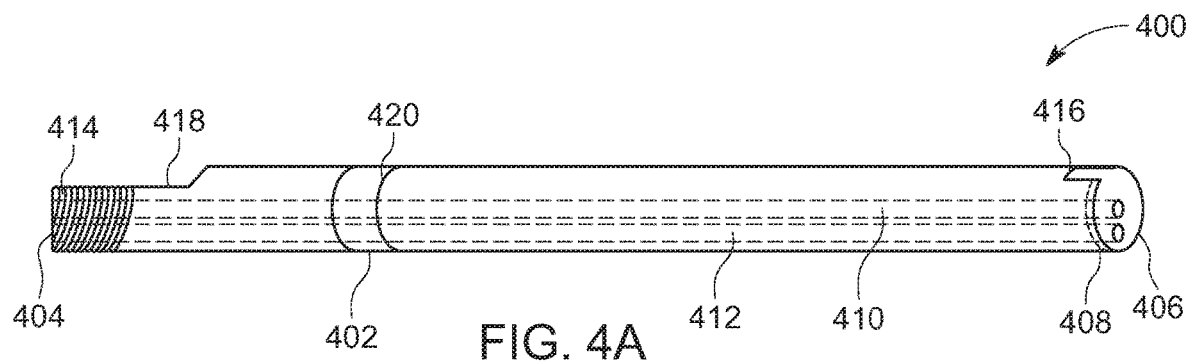
FIGS. 4A-4C illustrate diagrammatic views of a flexible pushing device of the said apparatus, in accordance with an example embodiment of the present disclosure.
Figure 4B:
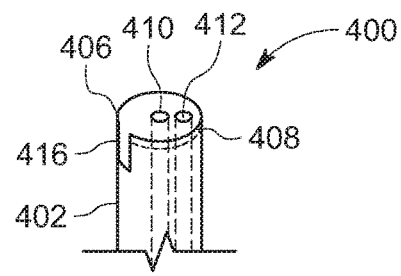
Figure 4C:
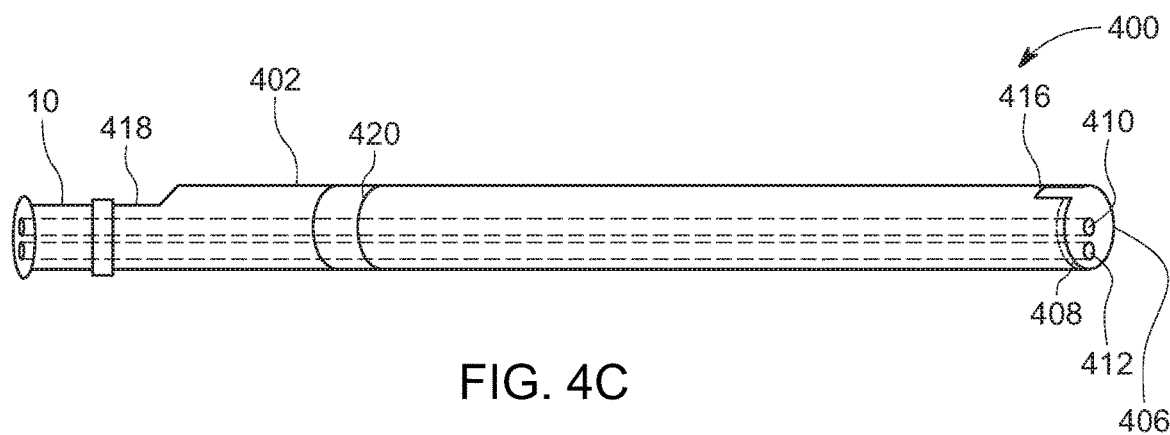

Referring to FIGS. 4A-4C in combination, illustrated is a flexible pushing device 400 to be used as a component of the said apparatus. The flexible pushing device 400 comprises a cylindrical body 402. Similar to the flexible pulling device 300, the body 402 of the flexible pushing device 400 may be made of any suitable surgical material as known in the art. The body 402 of the flexible pushing device 400 has a proximal end 404 and a distal end 406. The flexible pushing device 400 includes a concave-cup 408 (or a concave-cup shape) at the distal end 406 thereof. Such design of the flexible pushing device 400 with the concave-cup 408 at the distal end 406 helps to keep the flexible pushing device 400 external to the subcutaneous blood vessel. Such shape further facilitates pushing of the subcutaneous blood vessel secured with one of the pair of circumferential grooves 310 of the flexible pulling device 300, as discussed above.

The body 402 of the flexible pushing device 400 further includes a guidewire lumen 410. The guidewire lumen 410, in the flexible pushing device 400, is located centrally inside the body 402 of the flexible pushing device 400. The guidewire lumen 410 is generally in the form of a narrow cylindrical tube with sufficient diameter to receive the guidewire 100 therein. The flexible pushing device 400 is adapted to be co-axially arranged over the guidewire 100 by receiving the guidewire 100 in the guidewire lumen 410 therein. This allows for advancement and retraction of the flexible pushing device 400 over the guidewire 100 when inserted inside the human body. The flexible pushing device 400 further comprises a fluid lumen 412 extending between the two ends 404, 406 thereof to facilitate movement of air and fluids therein which would help with inversion and eversion of the subcutaneous blood vessel during the surgical procedure, as discussed later. In one embodiment, the fluid lumen 412 in the flexible pushing device 400 is arranged concentric to the guidewire lumen 410 therein. In another embodiment, the fluid lumen 412 in the flexible pushing device 400 is arranged adjacent to the guidewire lumen 410 therein.

In an embodiment, as illustrated in FIG. 4A, the flexible pushing device 400 further comprises some attachment means, such as threads 414 provided at the proximal end 404 thereof. The threads 414 allow for removably connecting an external adapter, such as a Luer lock or a Tuohy Borst adapter which in turn allow to attach a fluid loaded syringe therewith. FIG. 4C illustrates a depiction of the flexible pushing device 400 with the external adapter 10 attached therewith at the proximal end 404 thereof. Therefore, the threads 414 act as means which allows for infusion of fluids through the fluid lumen 412 in the flexible pushing device 400 for delivery to site at which the subcutaneous blood vessel is being harvested.

As illustrated, the flexible pushing device 400 further comprises a notch 416 located laterally at the distal end 406 thereof. The notch 416 may be in the form of a cut-out at a circumferential outer surface of the body 402 of the flexible pushing device 400. The notch 416 may have any suitable shape, such as V-notch or rectangular notch without any limitations. In the illustrated examples, the notch 416 is shown to have a rectangular shape. The notch 416 helps to engage side branches of the subcutaneous blood vessel therein, when the flexible pushing device 400 is inserted in the human body for harvesting of the subcutaneous blood vessel. The flexible pushing device 400 also comprises a flattened portion 418 at the proximal end 404 thereof. The flattened portion 418 may help to indicate radial orientation of the flexible pushing device 400, and thereby the notch 416 so as to facilitate positioning and engagement of the notch 416 with the side branches of the subcutaneous blood vessel. Alternatively, the radial orientation of the notch 416 may be indicated by one or more marks (such as the marks 212) independently or in addition to the flattened portion 418 in the flexible pushing device 400. Further, in an embodiment, the flexible pushing device 400 comprises one or more circumferential marks 420 and one or more longitudinal marks (not shown) thereon. The circumferential marks and the longitudinal marks may help to determine radial orientation and longitudinal positioning of the distal end 406 of the flexible pushing device 400 compared to other components of the apparatus, as will be discussed in more detail later in the description.

Figure 5:
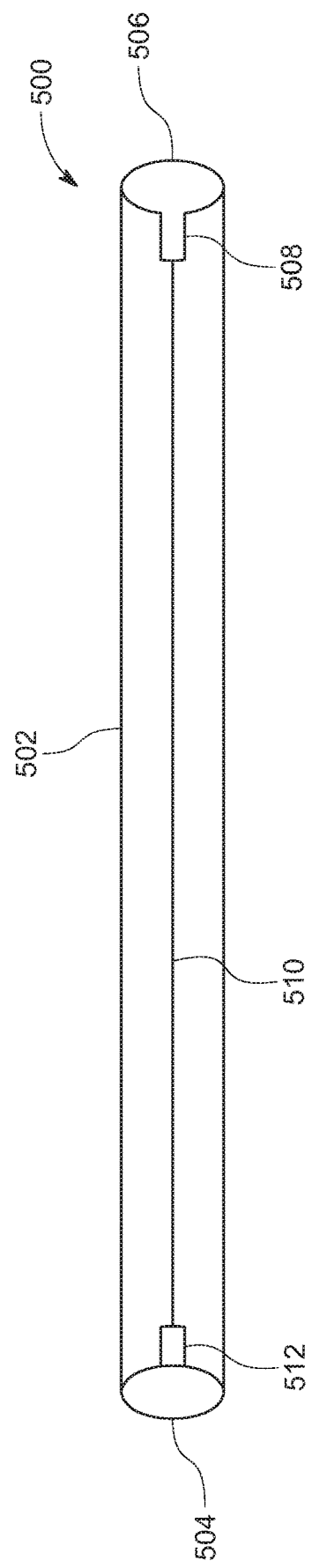
FIG. 5 illustrates a diagrammatic view of a flexible cutting sheath device of the said apparatus, in accordance with one or more embodiments of the present disclosure.

Referring to FIG. 5, illustrated is a flexible cutting sheath device 500 to be used as a component of the said apparatus. The flexible cutting sheath device 500 comprises a cylindrical body 502. The body 502 of the flexible cutting sheath device 500 may be made of any suitable surgical grade metallic material as known in the art. In general, the flexible cutting sheath device 500 is symmetrical, that is, the flexible cutting sheath device 500 has a symmetrical body 502. The body 502 of the flexible cutting sheath device 500 has a proximal end 504 and a distal end 506. The flexible cutting sheath device 500 is adapted to be introduced and to slide over the flexible pushing device 400. In an example, the body 502 of the flexible cutting sheath device 500 has a total length of about 50 cm. Further, the body 502 of the flexible cutting sheath device 500 has an internal diameter of about 7 mm. It may be appreciated that the given dimensions are exemplary only, and shall not be construed as limiting to the embodiments of the present disclosure.

The flexible cutting sheath device 500 comprises a notch 508 having sharpened edges or inserts located at the distal end 506 thereof. The notch 508, in the flexible cutting sheath device 500, may be in the form of a cut-out at a circumferential outer surface of the body 502 of the flexible cutting sheath device 500. The notch 508 may have any suitable shape, such as V-notch or rectangular notch without any limitations. In the illustrated examples, the notch 508 is shown to have a rectangular shape. The notch 508 helps to engage side branches of the subcutaneous blood vessel therein, when the flexible cutting sheath device 500 is inserted in the human body for harvesting of the subcutaneous blood vessel. Further, the notch 508 transect the side branches of the subcutaneous blood vessel engaged in the notch 406 of the flexible pushing device 400. This is achieved by rotation of the flexible cutting sheath device 500 and the flexible pushing device 400, or with respect to the flexible pushing device 400, in opposing directions.

In some embodiments, the flexible cutting sheath device 500 also comprises a longitudinal mark 510. The flexible cutting sheath device 500 also comprises a notch 512, which acts as an indicator notch, located at the proximal end 504 of the body 502 thereof. Herein, a radial orientation of the flexible cutting sheath device 500 is indicated by determining at least one of relative position of the notch 512 disposed at the proximal end 504 of the flexible cutting sheath device 500 and the longitudinal mark 510 of the flexible cutting sheath device 500 with respect to the one or more longitudinal marks in the flexible pushing device 400. Further, herein, the circumferential marks 420 on the flexible pushing device 400 help to indicate longitudinal positioning of the distal end 406 of the flexible pushing device 400 with respect to the distal end 506 of the flexible cutting sheath 500. In the above mentioned examples, the said marks may be in the form of reference points or dots provided at a particular radial or circumferential orientation on outer surfaces of the corresponding components and/or in the form of one or more reference lines extending on the outer surfaces of the corresponding components. It may be appreciated that other possible markings may be contemplated, such as, but not limited to, etchings or the like, without departing from the scope and the spirit of the present disclosure.

The present disclosure further provides method for harvesting of the subcutaneous blood vessel. In contrast to known techniques, such as open and endoscopic procedures, which are relatively lengthy procedures requiring extensive training and technical expertise and are not uniformly successful, the method of the present disclosure facilitate rapid vein harvesting using the apparatus in the form of a new endovascular device as discussed above. The method of the present disclosure provides minimally invasive techniques that can be completed rapidly and are easily taught to surgeons and their assistants and is performed with a high degree of success. Additionally, it avoids many of the complications that are associated with open surgical vein harvest procedures. Various embodiments and variants disclosed above, with respect to the aforementioned apparatus, apply mutatis mutandis to the present method for harvesting of a subcutaneous blood vessel. FIGS. 6A-6G depicts various steps involved in the said method and have been used to explain the procedure for the said method.

Figure 6A:
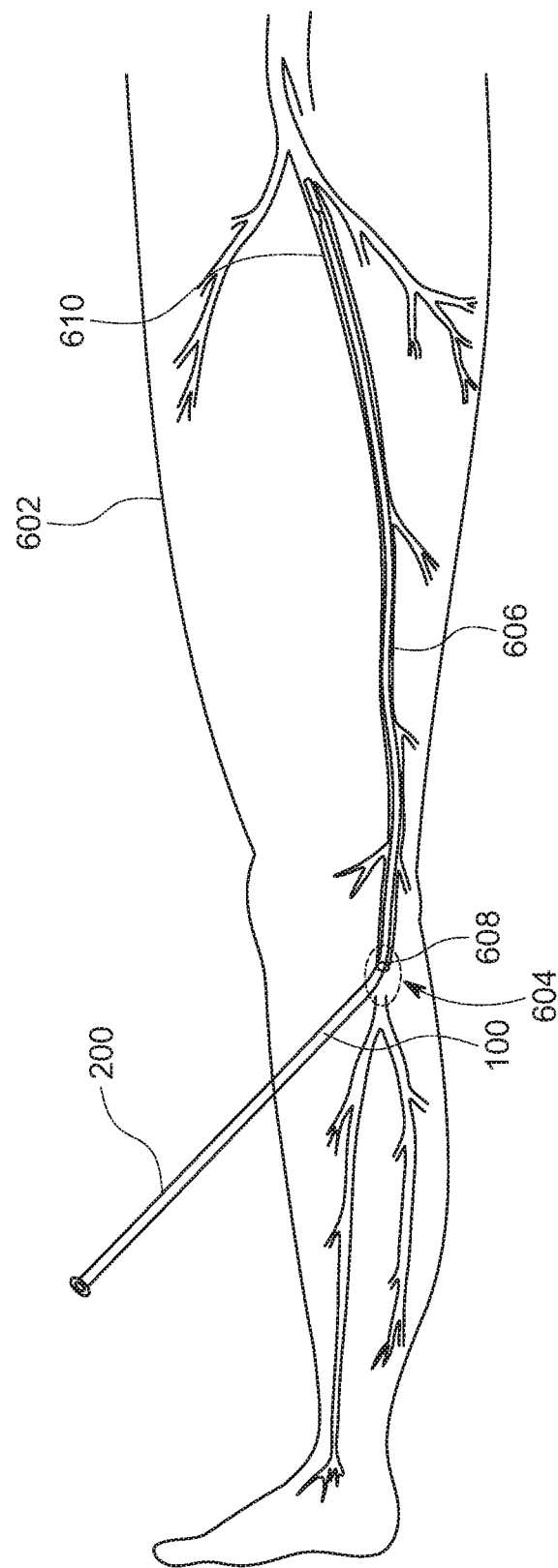
Figure 6B:
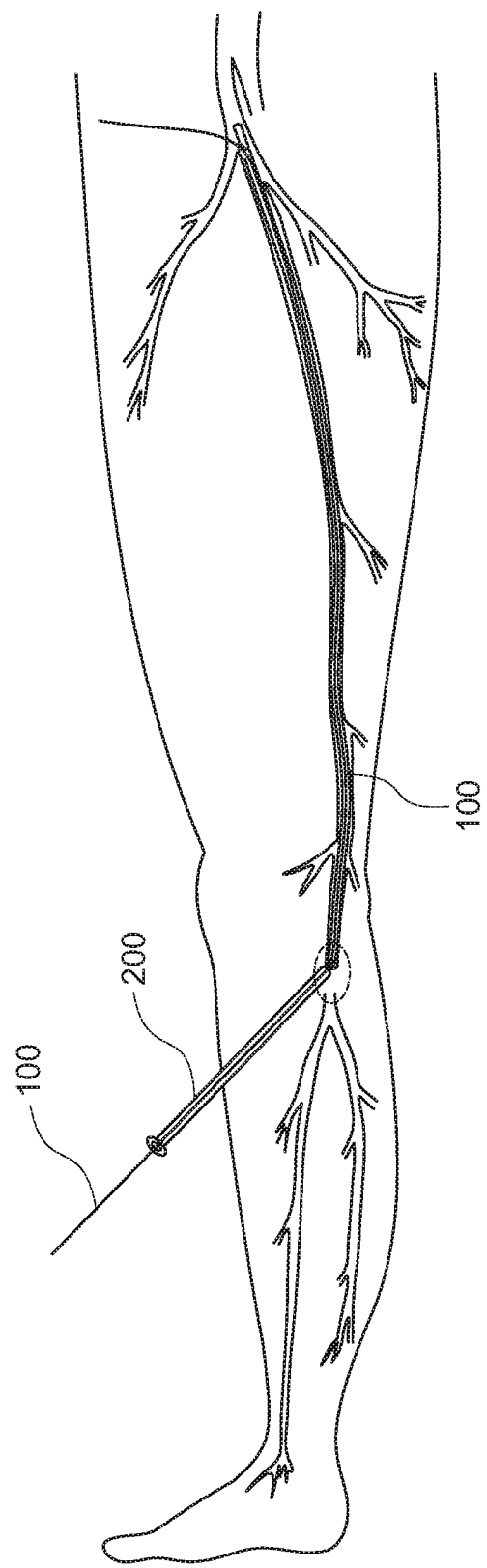
Figure 6C:
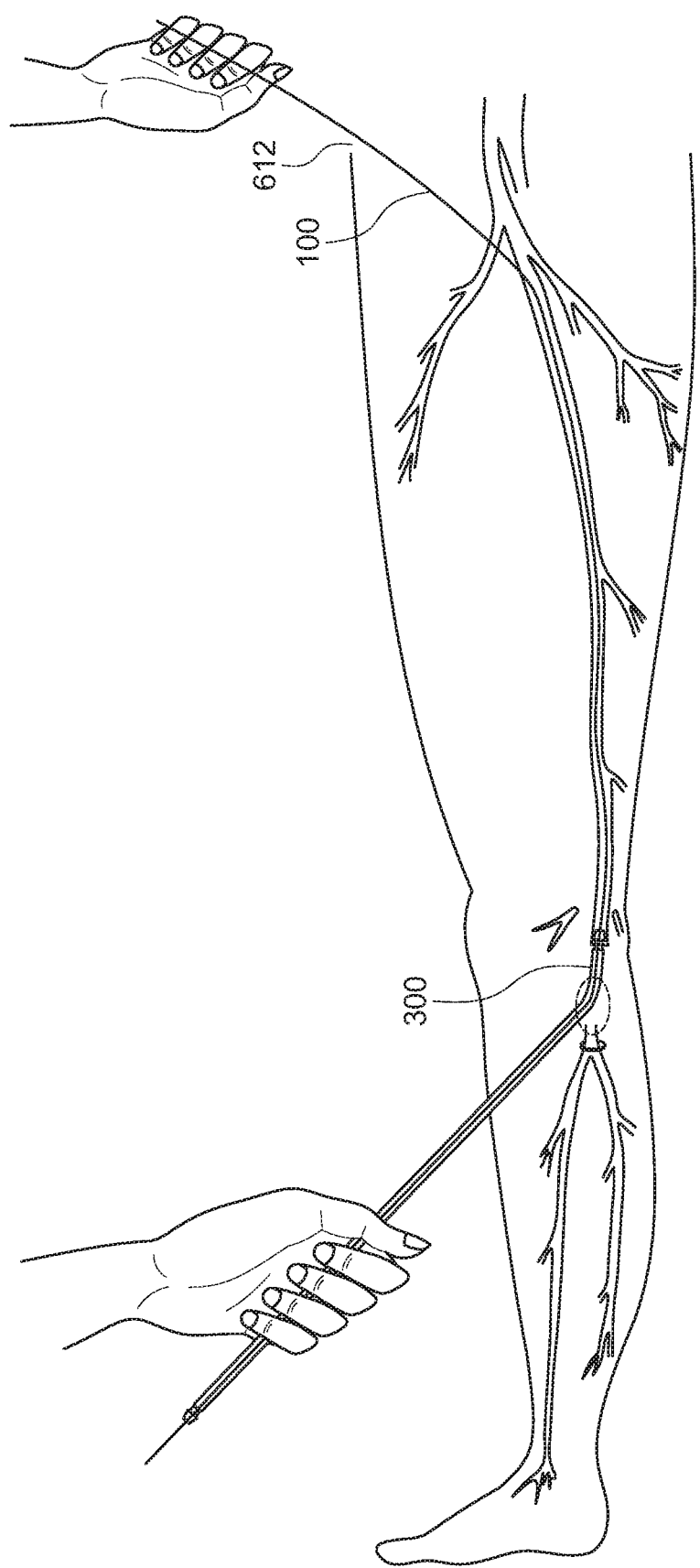

Referring to FIG. 6A, as depicted, the method includes, first, making a distal incision 604 in skin surface 602 over a distal end portion 608 of the subcutaneous blood vessel 606. Then, the subcutaneous blood vessel 606 exposed through the distal incision 604 is transected. Thereafter, the distal end portion 608 of the subcutaneous blood vessel 606 is ligated. Thereafter, the method includes inserting the intra-vascular catheter 200 into the subcutaneous blood vessel either alone or over a flexible vascular guidewire 606 through the distal end portion 608 and advancing the intra-vascular catheter 200 towards a proximal end portion 610 of the subcutaneous blood vessel 606. Subsequently, as depicted in FIG. 6B, the method includes receiving/inserting the angled guidewire 100 inside the intra-vascular catheter 200, extending therein from the distal end portion 608 to the proximal end portion 610 of the subcutaneous blood vessel 606. Herein, the lateral orifice 206 in the intra-vascular catheter 200 at the proximal end portion 610 of the subcutaneous blood vessel 606 is positioned, with the lateral orifice 206 facing anteriorly toward the skin surface 602. As depicted in FIG. 6B, the distal end 106 of the guidewire 100 is exited from the lateral orifice 206 in the intra-vascular catheter 200 to cause the angled tip 108 of the guidewire 100 to perforate the subcutaneous blood vessel 606 at a determined longitudinal and radial orientation, and making a proximal incision 612 in the skin surface 602 to allow the angled tip 108 of the guidewire 100 to exit therefrom. Further, as shown, the intra-vascular catheter 200 is withdrawn. Further, as shown in FIG. 6C, the method includes advancing the flexible pulling device 300 over the guidewire 100 from the proximal end 104 of the guidewire 100 to the distal end 106 thereof until the distal end 306 of the flexible pulling device 300 reaches near the proximal incision 612 in the skin surface 602 to be pulled out therefrom. Thereafter, the proximal end portion 610 of the subcutaneous blood vessel 606 is transected and ligated. During this process, the guidewire 100 is stabilized from the distal end 106, for instance by a separate individual.

Further, as shown in FIGS. 6D-6E, the method includes securing the distal end portion 608 of the subcutaneous blood vessel 606 to the circumferential groove 310 near the proximal end 304 of the flexible pulling device 300. Thereafter, the flexible pulling device 300 is pulled towards the proximal end portion 610 of the subcutaneous blood vessel 606 causing inversion thereof. Also, the flexible pushing device 400 is advanced over the guidewire 100 from the proximal end 104 of the guidewire 100 to the distal end 106 thereof to facilitate pushing of a folded edge of an inverted end of the subcutaneous blood vessel 606 secured with the circumferential groove 310 of the flexible pulling device 300 towards the proximal incision 612. In some cases, the method further includes introducing a fluid inside the fluid lumen 412 of the flexible pushing device 400 to facilitate a separation of the subcutaneous blood vessel 606 from surrounding tissues at the site of harvesting of the subcutaneous blood vessel 606. Herein, the fluid is introduced through the fluid lumen 412 in the flexible pushing device 400 by attaching a fluid source via an external adapter (such as, the external adapter 10 in FIG. 4C) connected to the threads 414 provided at the proximal end 404 of the flexible pushing device 400. The concave cup 408 at the distal end 406 of the flexible pushing device 400 assists with inversion of and separation of the subcutaneous blood vessel 606 being harvested from the surrounding tissues. The concave cup 408 of the flexible pushing device 400 is designed to work externally to the inverted end of the subcutaneous blood vessel being harvested at all times during the harvest. Hydro-dissection can be used to facilitate the process by attaching a screw on luer lock and "Tuohy-Borst" device to the exposed end of the flexible pushing device 400 and injecting saline (or medication as needed) to help separate the subcutaneous blood vessel 606 from the surrounding tissue.

Figure 6F:
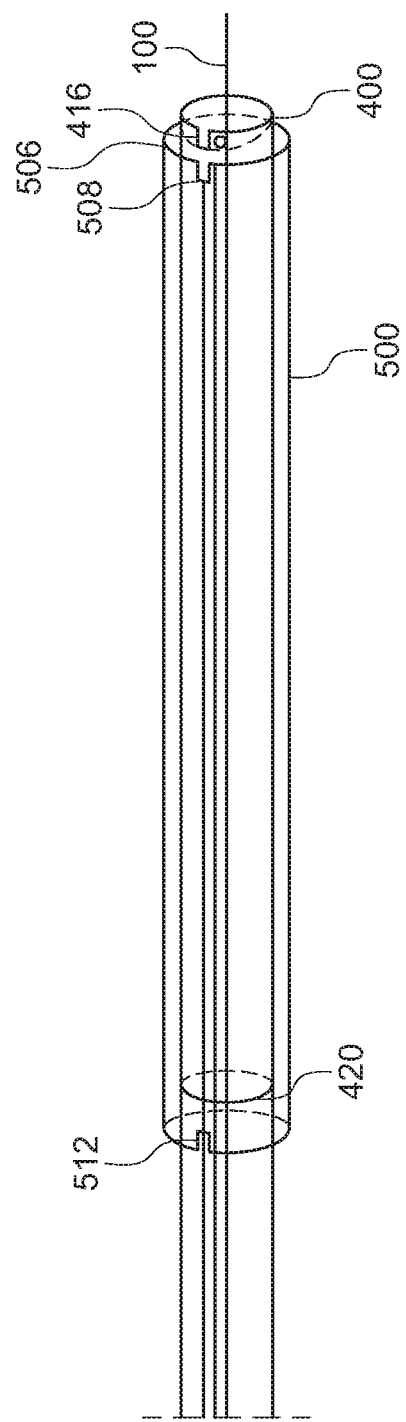

As depicted in FIG. 6F, the method further includes optionally advancing the flexible cutting sheath device 500 from the distal incision 604 towards the proximal end portion 610 of the subcutaneous blood vessel 606 by sliding over the flexible pushing device 400 to transect the side branches of the subcutaneous blood vessel 606 (as shown) engaged in the notch 416 of the flexible pushing device 400 by the notch 508 of the flexible cutting sheath device 500 by rotation of the flexible cutting sheath device 500 and the flexible pushing device 400 in opposing directions, to facilitate with harvesting of the subcutaneous blood vessel 606. Herein, the method also includes determining at least one of relative position of the notch 512 disposed at the proximal end 504 of the flexible cutting sheath device 500 and the longitudinal mark 510 of the flexible cutting sheath device 500 with respect to one or more longitudinal marks (including the notch 416) in the flexible pushing device 400 to indicate a radial orientation of the flexible cutting sheath device 500. Furthermore, an alignment of the distal end 506 of the flexible cutting sheath device 500 and the distal end 406 of the flexible pushing device 400 is accomplished by aligning the proximal end 504 of the flexible cutting sheath device 500 with the appropriate circumferential mark 420 on the flexible pushing device 400. Major side branches are engaged in the notch 416 of the flexible pushing device 400 and can be transected as needed by feeding the flexible cutting sheath device 500 over the flexible pushing device 400 until the longitudinal marks (including the notch 416) in the flexible pushing device 400 is visualized, indicating that the distal end 506 of the flexible cutting sheath device 500 is confluent with the distal end 406 of the flexible pushing device 400. The subcutaneous blood vessel 606 is then everted (pulled back distally) into its normal position and the distal ligature (securing the vein to the flexible pulling device 300) is removed.

Figure 6G:
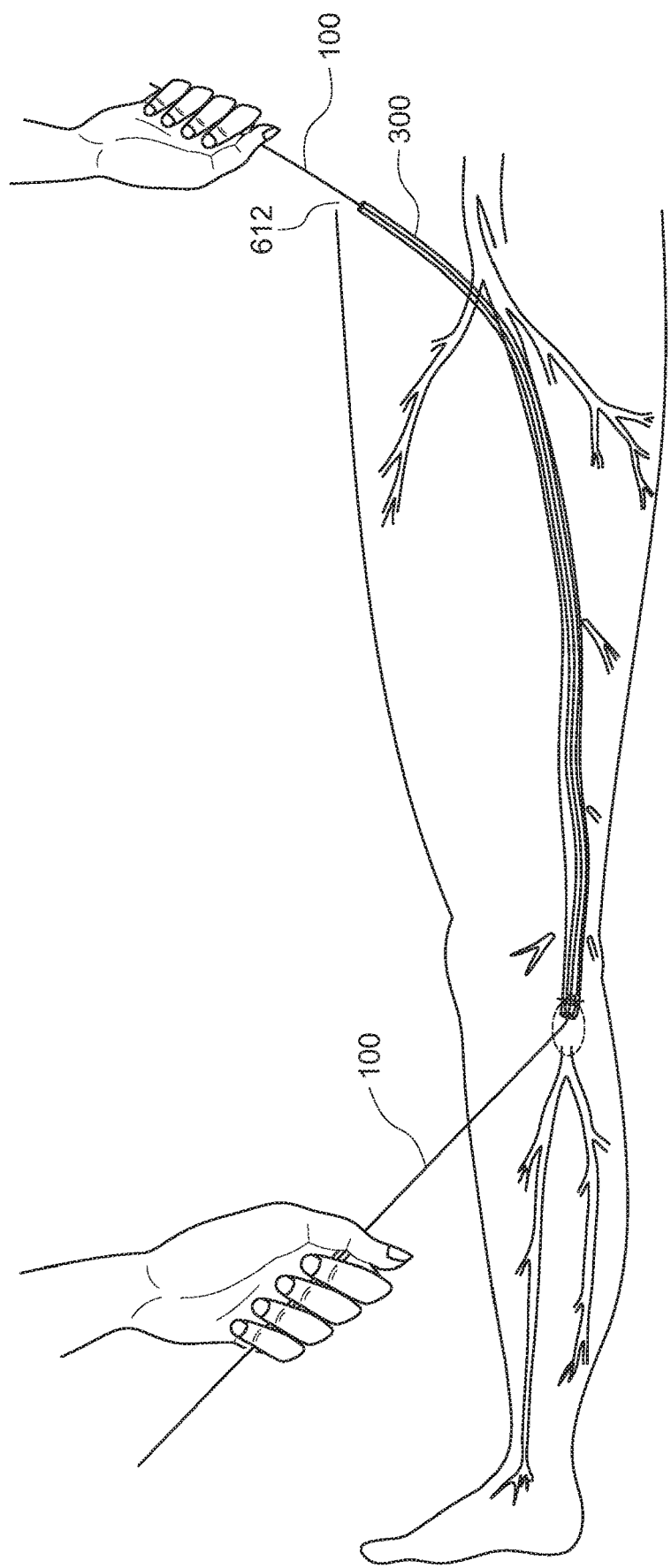

As illustrated in FIG. 6G, for pulling the subcutaneous blood vessel 606 into the normal position, the method includes removing the flexible pushing device 400 through the distal incision 604 by pulling the flexible pushing device 400 back towards the distal end portion 608 of the subcutaneous blood vessel 606 by advancing over the guidewire 100 from the distal end 106 of the guidewire 100 to the proximal end 104 thereof. Simultaneously, or subsequently, the flexible pulling device 300 is pushed/moved towards the distal incision 604 to evert the subcutaneous blood vessel 606 and position the distal end portion 608 of the subcutaneous blood vessel 606 proximate to the distal incision 606. Thereafter, the ligature (i.e. distal ligature) connecting the distal end portion 608 of subcutaneous blood vessel 606 is removed from the flexible pulling device 300.

Thereafter, the method further includes securing the proximal end portion 610 of the subcutaneous blood vessel 606 to the circumferential groove 310 near the distal end 306 of the flexible pulling device 300, and further pulling the flexible pulling device 400 towards the distal end portion 608 of the subcutaneous blood vessel 606 causing inversion thereof. Thereafter, the flexible pushing device 400 is advanced over the guidewire 100 from the distal end 106 of the guidewire 100 towards the proximal end 104 thereof to facilitate pushing of the subcutaneous blood vessel 606 towards the distal incision 604, while simultaneously pulling the subcutaneous blood vessel 606 using the flexible pulling device 606. Optionally, the flexible cutting sheath device 500 is advanced from the proximal incision 612 towards the distal end portion 608 of the subcutaneous blood vessel 606 by sliding over the flexible pushing device 300 to transect the side branches of the subcutaneous blood vessel 606 (as shown) engaged in the notch 416 of the flexible pushing device 400 by the notch 508 of the flexible cutting sheath device 500 by rotation of the flexible cutting sheath device 500 and the flexible pushing device 400 in opposing directions, to facilitate with harvesting of the subcutaneous blood vessel 606. Once the subcutaneous blood vessel 606 (i.e. the proximal end portion 610 of the subcutaneous blood vessel) becomes visible from the distal incision 604, the distal end portion 608 of the subcutaneous blood vessel 606 is circumferentially ligated and secured to the flexible pulling device 300 at the same groove 310 to which the proximal end 610 of the subcutaneous blood vessel 606 is secured. Both ends 608, 610 of the subcutaneous blood vessel 606 are then pulled as the flexible pushing device 400 is advanced and the subcutaneous blood vessel 606 is removed on the flexible pulling device 300 from the distal incision 604 of the patient and discarded or prepared for use as a bypass conduit. Further, it may be appreciated that any time during pushing of the subcutaneous blood vessel 606, the flexible pushing device 400 remains external or outside the subcutaneous blood vessel 606, while pushing the subcutaneous blood vessel 606.

Prior to removing the guidewire 100 from the harvest site, the catheter 200 can be advanced over the guidewire 100 to allow flushing or infusion of fluid and/or medication (e.g. thrombin, pro-coagulants). Hereinafter, all guidewires, catheters, and the flexible pushing device are removed. Skin incisions are sutured (or stapled) closed. A compressive wrap is applied to the harvest site (leg or arm) for 20-30 minutes to assist with hemostasis. It would be appreciated herein, that with the apparatus and the method of the present disclosure, the flexible pulling device 300 and the flexible pushing device 400 are operable in conjunction to cause inversion and eversion of the subcutaneous blood vessel 606 for harvesting without exposing an internal surface thereof.

The apparatus and method of the present disclosure are provided for percutaneous harvest/removal of an intact subcutaneous blood vessel (vein, occluded artery or prosthetic vessel) for disposal, because of vessel disease, disfunction, abnormalities or cosmetic reasons or for use as a bypass conduit or other medical purpose. The apparatus consists of five complimentary devices including the specialized vascular guidewire 100, the intra-vascular catheter 200 with the lateral orifice 206 (and optionally angled flap 208) to deflect the guidewire 100, the over-the-wire coaxial flexible pulling device 300, the coaxial flexible pushing device 400 with the infusion/working vein and tissue access channel(s), and the flexible cutting sheath device 500. The said devices in the apparatus work percutaneously and coaxially, in a complimentary fashion, sliding back and forth, inserted into the vein to be harvested, enabling rapid and largely atraumatic and intact harvest (removal) of a subcutaneous vein using specialized inversion/eversion and push/pull endovascular techniques.

While there have been described above the principles of the present invention in conjunction with an apparatus for harvesting of a subcutaneous blood vessel and a method therefore, it is to be understood that the foregoing description is made only by way of example and not as a limitation to the scope of the invention. Particularly, it is recognized that the teachings of the foregoing disclosure will suggest other modifications to those persons skilled in the relevant art. Such modifications may involve other features that are already known per se and which may be used instead of or in addition to features already described herein. Although claims have been formulated in this application to particular combinations of features, it should be understood that the scope of the disclosure herein also includes any novel feature or any novel combination of features disclosed either explicitly or implicitly or any generalization or modification thereof which would be apparent to persons skilled in the relevant art, whether or not such relates to the same invention as presently claimed in any claim and whether or not it mitigates any or all of the same technical problems as confronted by the present invention. The Applicant hereby reserves the right to formulate new claims to such features and/or combinations of such features during the prosecution of the present application or of any further application derived therefrom.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The exemplary embodiment was chosen and described in order to best explain the principles of the present disclosure and its practical application, to thereby enable others skilled in the art to best utilize the present disclosure and various embodiments with various modifications as are suited to the particular use contemplated.

What is claimed is:

1. An apparatus for harvesting of a subcutaneous blood vessel, comprising:
   a guidewire having a body with a proximal end and a distal end, the guidewire comprising an angled tip extending from the distal end of the body; an intra-vascular catheter adapted to be inserted into the subcutaneous blood vessel and receive the guidewire therein, extending therein from the proximal end to the distal end thereof, the intra-vascular catheter having a lateral orifice near a distal end thereof to allow for exiting of the guidewire therefrom and the angled tip thereof to perforate the subcutaneous blood vessel at a determined longitudinal and radial orientation and to be directed to a skin surface above the subcutaneous blood vessel to be retrieved through the skin surface;
   a flexible pulling device comprising a cylindrical body with a guidewire lumen and adapted to be co-axially arranged over the guidewire by receiving the guidewire in the guidewire lumen therein to allow for advancement and retraction thereof over the guidewire, the flexible pulling device having a pair of circumferential grooves, one adjacent to each end thereof, to allow for securing the subcutaneous blood vessel thereat; and
   a flexible pushing device comprising a cylindrical body with a guidewire lumen and adapted to be co-axially arranged over the guidewire by receiving the guidewire in the guidewire lumen therein to allow for advancement and retraction thereof over the guidewire, the flexible pushing device having a concave-cup at a distal end thereof to keep the flexible pushing device external to the subcutaneous blood vessel and to facilitate pushing of the subcutaneous blood vessel secured with one of the pair of circumferential grooves of the flexible pulling device,
   wherein the flexible pulling device and the flexible pushing device are operable in conjunction to cause inversion and eversion of the subcutaneous blood vessel for harvesting without exposing an internal surface thereof.

2. The apparatus of claim 1, wherein the guidewire comprises one or more marks to indicate the radial orientation thereof and a longitudinal positioning of the angled tip of the guidewire with respect to the lateral orifice of the intravascular catheter.

3. The apparatus of claim 2, wherein the angled tip extends at an angle in the range of 50 to 60 degrees with respect to a longitudinal portion of the body.

4. The apparatus of claim 1, wherein the intra-vascular catheter further comprises an angled movable flap, associated with the lateral orifice, for directing one or more of the guidewire and fluid to exit through the lateral orifice.

5. The apparatus of claim 1, wherein the guidewire lumen in the flexible pulling device is located centrally inside the flexible pulling device.

6. The apparatus of claim 1, wherein the flexible pulling device is symmetrical and has symmetrical tapered portions at each end thereof, with each of the pair of circumferential grooves being located adjacent to the tapered portions at each end thereof.

7. The apparatus of claim 1, wherein the flexible pushing device further comprises a fluid lumen extending between the guidewire lumen and a body of the intravascular catheter to facilitate movement of air and fluids therein and so as to facilitate inversion and eversion of the subcutaneous blood vessel.

8. The apparatus of claim 7, wherein the fluid lumen in the flexible pushing device is arranged concentric to the guidewire lumen.

9. The apparatus of claim 7, wherein the fluid lumen in the flexible pushing device is arranged adjacent to the guidewire lumen.

10. The apparatus of claim 7, wherein the flexible pushing device further comprises threads provided at a proximal end thereof to allow for removably connecting an external adapter for infusion of fluids through the fluid lumen in the flexible pushing device for delivery to a site at which the subcutaneous blood vessel is being harvested.

11. The apparatus of claim 1, wherein the flexible pushing device further comprises:
    a notch located laterally at the distal end thereof to engage side branches of the subcutaneous blood vessel; and
    a flattened portion at a proximal end thereof to indicate radial orientation of the notch so as to facilitate positioning and engagement of the notch with the side branches of the subcutaneous blood vessel.

12. The apparatus of claim 11 further comprising a flexible cutting sheath device adapted to be introduced and to slide over the flexible pushing device, the flexible cutting sheath device comprising a notch at a distal end thereof to transect the side branches of the subcutaneous blood vessel engaged in the notch of the flexible pushing device by rotation of the flexible cutting sheath device and the flexible pushing device in opposing directions.

13. The apparatus of claim 12, wherein the flexible pushing device further comprises one or more circumferential marks thereon to indicate longitudinal positioning and alignment of the distal end of the flexible pushing device with respect to the distal end of the flexible cutting sheath device.

14. The apparatus of claim 13, wherein the flexible pushing device comprises one or more longitudinal marks and the flexible cutting sheath device comprises one or more longitudinal marks, such that a radial orientation of the flexible cutting sheath device is indicated by determining a relative position of at least one of a notch disposed at a proximal end of the flexible cutting sheath device or the one or more longitudinal marks of the flexible cutting sheath device with respect to the one or more longitudinal marks of the flexible pushing device.

15. The apparatus of claim 1, wherein the body of the guidewire is coated with a hydrophilic coating.

16. A method for harvesting of a subcutaneous blood vessel, the method comprising the steps of:
(i) making a distal incision in a skin surface over a distal end portion of the subcutaneous blood vessel;
(ii) transecting the subcutaneous blood vessel exposed through the distal incision and ligating the distal end portion of the subcutaneous blood vessel;
(iii) inserting an intra-vascular catheter into the subcutaneous blood vessel through the distal end portion of the subcutaneous blood vessel and advancing the intra-vascular catheter towards a proximal end portion of the subcutaneous blood vessel;
(iv) receiving a guidewire having an angled tip inside the intra-vascular catheter, extending therein from the distal end portion to the proximal end portion of the subcutaneous blood vessel;
(v) positioning a lateral orifice in the intra-vascular catheter at the proximal end portion of the subcutaneous blood vessel, with the lateral orifice facing anteriorly toward the skin surface;
(vi) exiting the distal end of the guidewire from the lateral orifice in the intra-vascular catheter to cause the angled tip of the guidewire to perforate the subcutaneous blood vessel at a determined longitudinal and radial orientation and making a proximal incision in the skin surface to allow the angled tip of the guidewire to exit therefrom;
(vii) withdrawing the intra-vascular catheter;
(viii) advancing a flexible pulling device over the guidewire from the proximal end of the guidewire to the distal end thereof until a distal end of the flexible pulling device reaches near the proximal incision in the skin surface to be pulled out therefrom;
(ix) transecting and ligating the proximal end portion of the subcutaneous blood vessel;
(x) securing the distal end portion of the subcutaneous blood vessel to a circumferential groove near a proximal end of the flexible pulling device;
(xi) pulling the flexible pulling device towards the proximal end portion of the subcutaneous blood vessel causing inversion thereof;
(xii) advancing a flexible pushing device over the guidewire from the proximal end of the guidewire to the distal end thereof to facilitate pushing of a folded edge of an inverted end of the subcutaneous blood vessel secured with the circumferential groove of the flexible pulling device towards the proximal incision, keeping the flexible pushing device external to the subcutaneous blood vessel being harvested;
(xiii) introducing a fluid inside a fluid lumen of the flexible pushing device to facilitate a separation of the subcutaneous blood vessel from surrounding tissues; and
(xiv) advancing a flexible cutting sheath device from the distal incision towards the proximal end portion of the subcutaneous blood vessel by sliding over the flexible pushing device to transect the side branches of the subcutaneous blood vessel engaged in a notch of the flexible pushing device by a sharpened notch of the flexible cutting sheath device by rotation of the flexible cutting sheath device and the flexible pushing device in opposing directions, to facilitate with harvesting of the subcutaneous blood vessel.

17. The method of claim 16 further comprising the steps of:
(xv) everting the inverted portion of the subcutaneous blood vessel by pulling the flexible pulling device back over the guidewire towards the distal incision;
(xvi) disengaging the distal end portion of the subcutaneous blood vessel from the circumferential groove near the proximal end of the flexible pulling device;
(xvii) securing the proximal end portion of the subcutaneous blood vessel to a circumferential groove near the distal end of the flexible pulling device;
(xviii) further pulling the flexible pulling device towards the distal end portion of the subcutaneous blood vessel causing inversion thereof;
(xix) advancing the flexible pushing device over the guidewire from the distal end of the guidewire towards the proximal end thereof to facilitate inversion of subcutaneous blood vessel, and keeping the flexible pushing device external to the inverted subcutaneous blood vessel being harvested;
(xx) advancing the flexible cutting sheath device from the proximal incision towards the distal end portion of the subcutaneous blood vessel by sliding over the flexible pushing device to transect the side branches of the subcutaneous blood vessel engaged in the notch of the flexible pushing device by rotation of the flexible cutting sheath device and the flexible pushing device in opposing directions, to facilitate with harvesting of the subcutaneous blood vessel;
(xxi) securing the distal end portion of the subcutaneous blood vessel to the circumferential groove near the distal end of the flexible pulling device; and
(xxii) removing the flexible pulling device for removing the subcutaneous blood vessel, separated from the surrounding tissues, from the patient through the distal incision.

18. The method of claim 17 further comprising:
(xxiii) advancing the intra-vascular catheter over the guidewire; and
(xxiv) introducing one or more of fluids and medications in the intra-vascular catheter for flushing of or otherwise altering the site of the subcutaneous blood vessel.

19. The method of claim 16, wherein the step (xiii) comprises introducing the fluid through the fluid lumen in the flexible pushing device by attaching a fluid source via an external adapter connected to threads provided at a proximal end of the flexible pushing device.

20. The method of claim 16, wherein the step (xiv) comprises determining at least one of relative position of the notch disposed at a proximal end of the flexible cutting sheath device and a longitudinal mark of the flexible cutting sheath device with respect to one or more longitudinal marks in the flexible pushing device to indicate a radial orientation of the flexible cutting sheath device positioning the proximal end of the flexible cutting sheath device with respect to the one or more circumferential marks on the flexible pushing device so as to properly align the distal end of the flexible cutting sheath device with the distal end of the flexible pusher device.

* * * * *